United States Patent [19]

Cohnen et al.

[11] Patent Number: 4,777,181
[45] Date of Patent: Oct. 11, 1988

[54] ALPHA-2-ANTAGONISTIC SUBSTITUTED 4-FLUORO-ISOINDOLINES

[75] Inventors: Erich Cohnen, Jork; Ben Armah, Hamburg, both of Fed. Rep. of Germany

[73] Assignee: Beiersdorf AG, Hamburg, Fed. Rep. of Germany

[21] Appl. No.: 942,137

[22] Filed: Dec. 16, 1986

[30] Foreign Application Priority Data

Dec. 20, 1985 [DE] Fed. Rep. of Germany ....... 3545206

[51] Int. Cl.⁴ ................. A61K 31/415; C07D 403/12
[52] U.S. Cl. ..................................... 514/392; 548/316; 548/482
[58] Field of Search ................. 548/316, 482; 514/392

[56] References Cited

U.S. PATENT DOCUMENTS 4,221,798  9/1980  Cohnen ........................... 548/316 X
4,526,897  7/1985  Cohnen et al. ................. 548/316 X

FOREIGN PATENT DOCUMENTS 2816627  10/1979  Fed. Rep. of Germany ...... 548/316
2905501   8/1980  Fed. Rep. of Germany ...... 548/316
3133302   3/1983  Fed. Rep. of Germany ...... 548/316

OTHER PUBLICATIONS

*Arneimittel Forschung*, 32, II, 1982, pp. 1534–1540.
*Chemical Abstracts*, vol. 102, 1985, Ref. 17146 z.
*Chemical Abstracts*, vol. 96, 1982, Ref. 52154 e.
*Chemical Abstracts*, vol. 99, 1983, Ref. 99175 q.

*Primary Examiner*—Richard A. Schwartz
*Attorney, Agent, or Firm*—Sprung Horn Kramer & Woods

[57] ABSTRACT

Substituted 4-fluoro-isoindolines of the general formula I

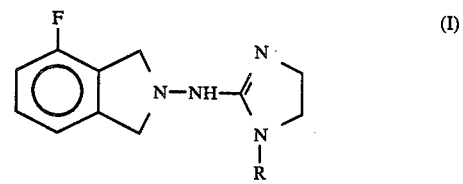

in which R denotes hydrogen or an acyl group, and their tautomeric forms and their acid addition salts have an alpha$_2$-antagonistic action.

17 Claims, No Drawings

ALPHA-2-ANTAGONISTIC SUBSTITUTED 4-FLUORO-ISOINDOLINES

The invention relates to new substituted 4-fluoro-isoindolines of the formula I

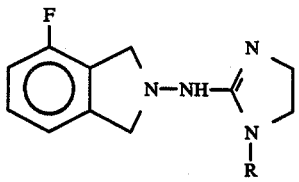

wherein R denotes hydrogen or an acyl group, and their tautomeric forms and acid addition salts thereof, and to processes for their preparation and their use and formulations containing these compounds.

For simplicity, the compounds according to the invention are defined in only one tautomeric form represented by formula I. However, the invention extends to all the tautomeric forms of the compounds.

Although pharmaceutically acceptable acid addition salts of the new compounds of the formula I and tautomeric forms thereof are preferred, all the salts lie within the scope of the invention. All the salts are useful for the preparation of the compounds, even if the particular salt is desired only as an intermediate product, such as, for example, if the salt is formed only for the purpose of purification or identification, or if it is used as an intermediate product in the preparation of a pharmaceutically acceptable salt, for example by ion exchange procedures.

German Offenlegungsschriften Nos. 2,816,627 and 2,905,501 and European Patent Application No. 72,954 disclose a large number of substituted isoindolines. However, the compounds according to the invention are neither described nor mentioned there.

The invention furthermore relates to the new compound 2-amino-4-fluoro-isoindoline, a process for its preparation and its use as an intermediate product for the preparation of the compounds of the formula I according to the invention.

Preferred acyl groups are substituted and unsubstituted straight-chain or branched alkylcarbonyl groups or alkanoyl groups and substituted and unsubstituted aroyl groups. Preferably, all these groups in each case have 1 to 7 carbon atoms, the phenyl group being the preferred aryl group. Particularly preferred alkylcarbonyl groups are those with 1 to 4 carbon atoms, in particular the formyl group, the acetyl group and the propionyl groups. The preferred aroyl radical is the benzoyl radical.

Acyl groups which are furthermore preferred are substituted and unsubstituted cycloalkylcarbonyl groups, preferably those with 4 to 7 carbon atoms. Cyclopropyl and cyclohexyl rings are preferred.

Preferred substituents of the acyl groups, in particular the alkylcarbonyl groups, are firstly alkoxy groups, preferably those with 1 to 4 carbon atoms and particularly preferably methoxy and ethoxy groups, and secondly cycloalkyl groups with preferably 3 to 6 carbon atoms in the ring system, preferably with a cyclopropyl or cyclohexyl ring, and thirdly aryl groups, in particular phenyl groups. Substituted acetyl groups are particularly preferred.

The following compounds according to the invention and acid addition salts thereof with a high therapeutic effect are particularly preferred:

4-fluoro-2-(2-imidazolin-2-ylamino)-isoindoline and the following acyl derivatives: 4-fluoro-2-(1-acetyl-2-imidazolin-2-ylamino)-isoindoline, 4-fluoro-2-(1-propionyl-2-imidazolin-2-ylamino)-isoindoline, 4-fluoro-2-(1-methoxyacetyl-2-imidazolin-2-ylamino)-isoindoline, 4-fluoro-2-(1-isobutyroyl-2-imidazolin-2-ylamino)-isoindoline, 4-fluoro-2-(1-cyclopropylcarbonyl-2-imidazolin-2-ylamino)-isoindoline, 4-fluoro-2-(1-phenylacetyl-2-imidazolin-2-ylamino)-isoindoline and 4-fluoro-2-(1-benzoyl-2-imidazolin-2-ylamino)-isoindoline.

Of these compounds, 4-fluoro-2-(2-imidazolin-2-ylamino)-isoindoline and its acid addition salts are particularly preferred. The compound is distinguished by a particularly high selectivity and efficacy.

The compounds of the formula I according to the invention and their physiologically acceptable acid addition salts are therapeutic active compounds, have a high pharmacological action and are useful medicaments. Thus, they exhibit a pharmacological action spectrum which was not to be predicted and is therapeutically useful and on the basis of their alpha$_2$-antagonistic action can be used as coronary therapeutics. In particular, because of their vasodilating properties, they can be used as antihypertensives for pulmonary or arterial hypertension. The substances according to the invention are furthermore suitable for the treatment of migraine, angina pectoris, Raynaud's disease, asthma and metabolic disorders, diabetes and obesity. The compounds of the formula I and their salts also have platelet aggregation-inhibiting properties.

The compounds of the present invention can be used orally or parenterally. The individual dose is 1 to 50 mg in humans, preferably 1 to 5 mg. This dosage is preferred for treatment of hypertension.

The daily dose, as is customary for alpha-antagonists, is to be matched according to the individual, because it depends on the receptor sensitivity and the sympathetic tone of the patient. The treatment is advantageously started with lower doses and then increased.

The invention provides pharmaceutical compositions which contain a compound of the formula I or pharmaceutically acceptable salts thereof, together with a pharmaceutically acceptable diluent or excipient.

The compounds according to the invention can be administered by themselves or as a mixture with customary pharmaceutically acceptable diluents or excipients and if appropriate with other auxiliaries, and administered, for example, orally or parenterally. They can be administered orally in the form of tablets, coated tablets, suppositories, powders, syrups, suspensions and liquids or parenterally in the form of solutions or suspensions. Preparations to be administered orally can contain one or more additives, such as sweeteners, aromatizing agents, dyestuffs and preservatives. Tablets can contain the active compound mixed with customary pharmaceutically acceptable auxiliaries, for example inert diluents, such as calcium carbonate, sodium carbonate, lactose and talc, granulating agents and agents which promote the disintegration of the tablets on oral administration, such as starch or alginic acid, binders, such as starch or gelatine, and lubricants, such as magnesium stearate, stearic acid and talc.

Examples of suitable excipients are lactose, gelatine, maize starch, stearic acid, ethanol, propylene glycol, ethers of tetrahydrofuryl alcohol and water.

The tablets can be coated by known procedures in order to delay disintegration and absorption in the gastrointestinal tract, which means that the activity of the active compound can extend over a longer period of time. The active compound in the suspensions can likewise be mixed with auxiliaries which are customary for the preparation of such compositions, for example suspending agents, such as methylcellulose, tragacanth or sodium alginate, wetting agents, such as lecithin, polyethylene stearate and polyoxyethylene sorbitan monooleate, and preservatives, such as ethyl parahydroxybenzoate. Capsules can contain the active compound as a single constituent or mixed with a solid diluent, such as calcium carbonate, calcium phosphate or kaolin. The injectable preparations are likewise formulated in a manner which is known per se. The pharmaceutical preparations can contain the active compound in an amount of 0.1 to 90%, in particular 1 to 90%, the remainder being an excipient or additive. Solid preparations, such as tablets and capsules, are preferred in respect of the preparation and administration. The preparations preferably contain the active compound in an amount of 2 mg.

The object of the invention was to discover the surprisingly selectively and highly active compounds according to the invention, taking into account the large number of compounds of similar structure.

The compounds according to the invention, that is to say the compound 4-fluoro-2-(2-imidazolin-2-ylamino)-isoindoline and acyl derivatives thereof, have these outstanding properties in comparison with other compounds of similar structure in a manner which could not be predicted. It is assumed that these particular specific actions depend on the particular structure of the compounds according to the invention.

It is assumed that this surprising superior activity of the new compounds is based on the 4-fluorine substitution of 2-(2-imidazolin-2-ylamino)-isoindoline.

The new compounds of the formula I can be prepared by the following processes:

(a) By reaction of 2-amino-4-fluoro-isoindoline with a compound of the formula II

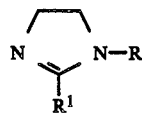

(II)

in which R¹ denotes a group which can be replaced nucleophilically, such as the alkylthio group or a halogen atom, and R denotes a hydrogen atom or an acyl group as described above. Preferred acyl groups are acetyl, propionyl or butyryl groups. The acetyl group is preferred. The reaction is carried out in an alcohol, advantageously n-amyl alcohol, as the solvent, at the boiling point.

Methylthio compounds, for example in the form of their hydriodides, are particularly suitable for this reaction.

To prepare the compound of the formula I according to the invention in which R denotes hydrogen, these acyl groups can be split off with dilute acids at room temperature (b) By reaction of 2-amino-4-fluoro-isoindoline with a compound of the general formula III

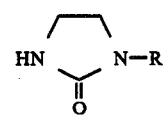

(III)

in which R denotes an acyl group with the meaning given.

The reaction is carried out, for example, with a 1-acyl-imidazolin-2-one in the presence of at least 2 mol of phosphorus oxytrichloride at temperatures of 50°–100° C. over a reaction time of 70 to 4 hours.

Preferred acyl groups have 2 to 4 carbon atoms.

After the condensation, the acyl group can be split off hydrolytically with acids or bases, preferably by heating in ethanol under acid conditions.

The acyl derivatives according to the invention can also be obtained from the resulting 4-fluoro-2-(2-imidazolin-2-ylamino)-isoindoline with acylating agents, such as acyl halides in which the acyl group has the abovementioned meaning.

The new compound 2-amino-4-fluoro-isoindoline is obtained by the following process:

The phthalimide of the formula (IV)

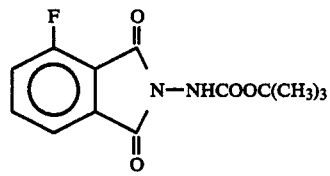

(IV)

is obtained from 4-fluoro-phthalic anhydride and tert.-butyl carbazate by heating in a suitable solvent, and is converted into the isoindoline of the formula (V)

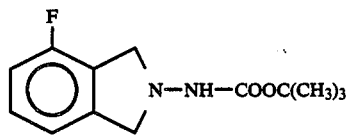

(V)

by reduction with lithium aluminium hydride.

The tert.-butoxycarbonyl group is removed by hydrolysis with mineral acids to give 2-amino-4-fluoro-isoindoline.

The starting compounds of the formulae II and III are known or can be obtained by known processes.

The compounds of the general formula I can be isolated from the reaction mixtures either as bases or in the form of their salts. As bases, they can be converted into the salts with suitable inorganic or organic acids by known processes.

Physiologically acceptable salts of the compounds of the formula I are preferred. Inorganic acids which are suitable for these are, for example, hydrogen halide acids, for example hydrochloric acid or sulphuric acid, and suitable organic acids are, for example, fumaric acid, maleic acid, citric acid and tartaric acid. For the preparation, the alcoholic solution of a suitable acid is added to a hot alcoholic solution of the base and, after addition of ether, the salt is obtained.

Particularly preferred salts are: hydrochlorides, hydrogen sulphates, hydrogen phosphates, fumarates, maleates, lactates and citrates.

The following examples serve to illustrate the invention:

EXAMPLE 1

4-Fluoro-2-(2-imidazolin-2-ylamino)-isoindoline 6.0 g (0.03 mol) of 2-amino-4-fluoro-isoindoline hydrochloride and 4.5 g (0.035 mol) of 1-acetyl-imidazolin-2-one are heated at 100° C. in 70 ml of phosphorus oxytrichloride for 4 hours. After removal of the $POCl_3$ in vacuo, the residue is dissolved in 100 ml of ethanol and the solution is heated at the boiling point for 3 hours. The solvent is distilled off, 5N NaOH is added to the residue and the crude base is extracted with methylene chloride. Recrystallization from toluene gives 5.9 g of 4-fluoro-2-(2-imidazolin-2-ylamino)-isoindoline.

Melting point 168°–170° C.

EXAMPLE 2

4-Fluoro-2-(2-imidazolin-2-ylamino)-isoindoline maleate 2.0 g of the base (Example 1) are dissolved in 100 ml of hot ethyl acetate and a hot solution of 1 g of maleic acid in ethyl acetate is added.

Yield: 2.6 g

Melting point 189°–191° C.

EXAMPLE 3

2-Amino-4-fluoro-isoindoline (a) 11.6 g (0.07 mol) of 3-fluoro-phthalic anhydride are suspended in 200 ml of o-xylene and 9.3 g (0.07 mol) of tert.-butyl carbazate are added in portions. The mixture is heated for 2 hours, water being distilled off. After cooling, 17.1 g of 3-fluoro-N-(tert.-butoxycarbonyl)-amino-phthalimide crystallize out.

Melting point 183°–184° C.

(b) 5.6 g of $LiAlH_4$ are suspended in 70 ml of absolute tetrahydrofuran. A solution of 15.9 g (0.06 mol) of the phthalimide from stage (a) in 150 ml of THF is added dropwise at 30°–45° C., under $N_2$. The mixture is stirred at room temperature for a further 3 hours and 20 ml of 2N NaOH are then added dropwise. The precipitate is filtered off and the solvent is stripped off in vacuo. The residue is extracted with toluene under the influence of heat. After evaporation of the toluene, 8.6 g of 4-fluoro-N-tert.-butoxycarbonylamino-isoindoline are obtained as a crystalline substance, which is recrystallized from cyclohexane.

Melting point 106°–108° C.

(c) 3.8 g of 4-fluoro-N-tert.-butoxycarbonylamino-isoindoline are introduced into 30 ml of concentrated hydrochloric acid at room temperature. The mixture is subsequently stirred at room temperature for 1 hour and the solvent is then distuilled off in vacuo. The residue is treated with hot i-propanol; after cooling to 10° C., the precipitate is filtered off with suction. 2.1 g of 2-amino-4-fluoro-isoindoline hydrochloride are obtained.

Melting point 208°–210° C. (decomposition).

EXAMPLE 4

4-Fluoro-2-(1-acetyl-2-imidazolin-2-ylamino)-isoindoline 33.2 g (0.18 mol) of 2-amino-4-fluoro-isoindoline hydrochloride and 24.8 g (0.19 mol) of 1-acetyl-imidazolin-2-one are heated to 160° C. in 70 ml of phosphorus oxytrichloride for 4 hours. The excess $POCl_3$ is removed in vacuo, the residue is poured onto ice and the mixture is rendered alkaline with 10% strength NaOH. The acetyl compound is extracted with $CH_2Cl_2$ and the methylene chloride phase is washed several times with water. After removal of the solvent, 30.5 g of 4-fluoro-2-(1-acetyl-2-imidazolin-2-ylamino)-isoindoline are obtained.

Melting point 121°–123° C. (toluene)

EXAMPLE 5

Preparation of tablets

Tablets which contain the constituents shown below are produced by known procedures. These tablets are suitable for the treatment of the abovementioned illnesses in a dosage amount of 1 or 2 tablets once or twice daily.

|  | Tablet A | Tablet B |
| --- | --- | --- |
| 4-Fluoro-2-(2-imidazolin-2-ylamino)-isoindoline maleate | 2 mg | 5 mg |
| Lactose | 90 mg | 90 mg |
| Maize starch | 5 mg | 5 mg |
| Magnesium stearate | 1 mg | 1 mg |

EXAMPLE 6

Preparation of ampoules

Ampoules which contain the constituents mentioned below can be produced in a known manner. The active compound and sodium chloride are dissolved in water and glass ampoules are filled with the solution, under nitrogen. These ampoules are suitable for the treatment of the abovementioned illnesses in a dosage amount of 0.5 mg i.v. once or twice daily.

| 4-Fluoro-2-(2-imidazolin-2-ylamino)-isoindoline maleate | 0.5 mg |
| --- | --- |
| Sodium chloride | 18 mg |
| Distilled water to | 2.0 g |

We claim:

1. A substituted 4-fluoro-isoindoline compound of the formula (I)

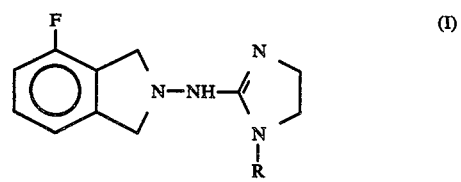

in which R denotes hydrogen or a carboxylic acid acyl group selected from the group consisting of an alkylcarbonyl, cycloalkylcarbonyl or aroyl group having 1 to 7 carbon atoms in the alkyl, cycloalkyl or aryl moiety, or a tautomeric form thereof or an acid addition salt thereof.

2. 4-Fluoro-2-(2-imidazolin-2-ylamino)-isoindoline.

3. 4-Fluoro-2-(1-acetyl-2-imidazol-2-ylamino)-isoindoline.

4. A compound according to claim 1, wherein the alkylcarbonyl or aroyl group is optionally independently substituted by at least one of $C_{1-4}$-alkoxy, $C_{3-6}$-cycloalkyl and phenyl.

5. 2-Amino-4-fluoro-isoindoline.

6. A compound according to claim 4, wherein the alkylcarbonyl group contains 1 to 4 carbon atoms.

7. A compound according to claim 4, wherein the alkylcarbonyl group is selected from the group consisting of a formyl group, an acetyl group and a propionyl group.

8. A compound according to claim 4, wherein the aroyl group is a benzoyl radical.

9. A compound according to claim 1, wherein the cycloalkylcarbonyl group contains 4 to 7 carbon atoms.

10. A compound according to claim 1, wherein the cycloalkylcarbonyl group contains a ring selected from the group consisting of a cyclopropyl ring and a cyclohexyl ring.

11. A compound according to claim 4, wherein the alkoxy group is selected from the group consisting of a methoxy group and an ethoxy group.

12. A compound according to claim 4, wherein for the cycloalkyl group the ring is selected from the group consisting of a cyclopropyl ring and a cyclohexyl ring.

13. A pharmaceutical composition having $\alpha_2$-antagonistic action containing as an active ingredient a pharmaceutically effective amount of a compound of claim 1 in admixture with an inert pharmaceutical carrier.

14. A medicament having $\alpha_2$-antagonistic action in unit dosage form comprising a pharmaceutically effective amount of a compound of claim 1 and an inert pharmaceutical carrier.

15. A medicament according to claim 14, in the form of a tablet, suppository, powder, syrup, suspension or liquid.

16. A method of treating a patient suffering from diabetes, comprising administering to the patient an effective amount of a substituted 4-fluoro-isoindoline compound of the formula (I)

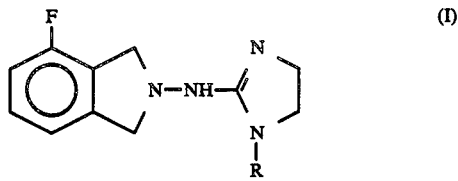

in which R denotes hydrogen or a carboxylic acid acyl group selected from the group consisting of an alkylcarbonyl, cycloalkylcarbonyl or aroyl group having 1 to 7 carbon atoms in the alkyl, cycloalkyl or aryl moiety, or a tautomeric form thereof or an acid addition salt thereof.

17. A method according to claim 16 wherein the compound is selected from the group consisting of 4-fluoro-2-(2-imidazolin-2-ylamino)-isoindoline and 4-fluoro-2-(1-acetyl-2-imidazolin-2-ylamino)-isoindoline.

* * * * *